United States Patent
Lee et al.

(10) Patent No.: US 7,875,194 B2
(45) Date of Patent: Jan. 25, 2011

(54) METHOD FOR MANUFACTURING HYDROGEN SENSORS USING PD NANO WIRE

(75) Inventors: Woo Young Lee, Seoul (KR); Kye Jin Jeon, Suwon (KR); Eun Song Yi Lee, Bucheon-si (KR)

(73) Assignee: Industry - Academic Cooperation Foundation, Yonsei University, Seodaemun-gu, Seoul (KR)

(*) Notice: Subject to any disclaimer, the term of this patent is extended or adjusted under 35 U.S.C. 154(b) by 682 days.

(21) Appl. No.: 11/959,959

(22) Filed: Dec. 19, 2007

(65) Prior Publication Data
US 2010/0096071 A1   Apr. 22, 2010

(30) Foreign Application Priority Data
Dec. 27, 2006   (KR) .................. 10-2006-0135209

(51) Int. Cl.
*C23F 1/00* (2006.01)
(52) U.S. Cl. ............................. 216/2; 73/23.2
(58) Field of Classification Search ............. 216/2; 73/23.2
See application file for complete search history.

(56) References Cited

U.S. PATENT DOCUMENTS 7,104,111 B2 * 9/2006 Monty et al. .................. 73/23.2

FOREIGN PATENT DOCUMENTS

| KR | 2005-0039016 | 4/2005 |
|---|---|---|
| KR | 2005-0122587 | 12/2005 |
| KR | 2006-0015629 | 2/2006 |
| KR | 2006-0088700 | 8/2006 |
| WO | 2004/020978 A2 | 3/2004 |

OTHER PUBLICATIONS

Yeonho Im et al., "Investigation of a Single Pd Nanowire for Use As a Hydrogen Sensor", Small 2006, 2, No. 3, pp. 356-358.
Bangar Ma et al., "Controlled Growth of a Single Palladium Nanowire Between Micorfabricated Electordes", Chemistry of Metals 16(24):4955-4959 Nov. 30, 2004 (Abstract).
Yin Dh et al. "Tunable Metallization by Assembly of Metal Nanoparticles in Polymer Thin Films by Photo—or Electron Beam Lithography", Langmuir 21(20):9352-9358 Sep. 27, 2005 (Abstract).

* cited by examiner

*Primary Examiner*—Roberts Culbert
(74) *Attorney, Agent, or Firm*—Lexyoume IP Group, PLLC.

(57) ABSTRACT

Disclosed is a method for manufacturing a hydrogen sensor using Pd nano-wires. The method includes steps of forming an external electrode pattern on a substrate applying a first resin layer to the substrate and forming a resin layer nano-channel pattern; depositing Pd on the substrate having the nano-channel pattern, by sputtering, and removing the first resin layer to form Pd nano-wires; applying a second resin layer to the substrate having the Pd nano-wires, and forming a resin layer pattern on the external electrode pattern, at opposing ends of the Pd nano-wires, and at predetermined positions between the external electrode pattern and the opposing ends of the Pd nano-wires; and depositing conductive metal on the resin layer pattern and removing the resin layer pattern, thereby electrically connecting the external electrode pattern to the Pd nano-wires.

10 Claims, 6 Drawing Sheets

(a)     (b)

METHOD FOR MANUFACTURING HYDROGEN SENSORS USING PD NANO WIRE

BACKGROUND OF THE INVENTION

1. Field of the Invention

The present invention relates to a method for manufacturing a hydrogen sensor using Pd nano-wires, and more particularly, to a method for manufacturing a micro-scale and high sensitive hydrogen sensor using Pd nano-wires, which are prepared by sputtering.

2. Description of the Prior Art

To date, in order to solve environmental pollution such as global warming attributable to the use of fossil fuel and energy shortage attributable to the exhaustion of fossil fuel, a number of alternative energy resources are under the development. As one of the main solutions, research on hydrogen energy is being regarded more important.

Hydrogen energy can advantageously overcome both of the above-mentioned problems. As another merit, hydrogen energy can overcome the finiteness of fossil fuel since it can be produced from and recycled to infinite water. Furthermore, the use of hydrogen does not produce pollutants except for a faint amount of $NO_x$. Therefore, in order to overcome the problems such as energy shortage and environmental pollution that the human beings confront, the development of hydrogen energy is being accelerated. Accordingly, the use of hydrogen energy is expected to spread to various fields in addition to the present limited fields, which are generally treated by experts.

However, on considerations that hydrogen is highly explosive, especially, in the case of the leakage, the use of hydrogen as an energy source in various fields including hydrogen fuel cell vehicles can be hardly realized unless hydrogen is carefully and stably managed. Therefore, together with the development of hydrogen energy, it is essential to develop a hydrogen gas sensor capable of detecting hydrogen leakage as early as possible.

To the present, various hydrogen sensors have been developed. Examples of these sensors may include a sensor using catalytic combustion or a heat wire, a sensor using a $SiO_2$ or AlN metal oxide (nitride) semiconductor, and a sensor using a Schottky barrier diode having two poles, in which SiC, GaN or the like is applied to bulk Pd or Pt. However, these hydrogen sensors have drawbacks such as a big size, a complex structure and a high cost. Furthermore, since these hydrogen sensors operate at a high temperature of 300° C. or more, they have drawbacks such as high power consumption and low selectivity for hydrogen.

Accordingly, researches on materials and structures of hydrogen sensors capable of optimizing performance are being carried out. Representative examples may include the application of nano-technology to a sensor device and the use of a nano-material as a sensor material. The nano-material has a nano-scale particle size (from several nanometers to tens of nanometers), and thus its physical properties are maximized on the surface of the particle. Hence, the nano-material can be advantageously used as a catalyst based on surface reaction or a detecting material for a sensor. Furthermore, when a sensor is developed using the nano-material, the sensor is expected to have various merits such as micro size, ultra high sensitivity and operability in an ultra low power mode. Accordingly, studies on such sensors are being actively carried out these days.

SUMMARY OF THE INVENTION

The present invention has been made to solve the foregoing problems with the prior art and therefore an object of the present invention is to provide a method for manufacturing a hydrogen sensor using Pd nano-wires, which has merits such as micro size, operability in an ultra low power mode and ultra high sensitivity.

According to an aspect of the invention for realizing the object, the invention provides a method for manufacturing a hydrogen sensor using Pd nano-wires. The method includes steps of:

Forming an external electrode pattern on a substrate;

Applying a first resin layer to the substrate, and forming a resin layer nano-channel pattern;

Depositing Pd on the substrate having the nano-channel pattern by sputtering, and removing the first resin layer to form Pd nano-wires;

Applying a second resin layer on the substrate having the Pd nano-wires, and forming a resin layer pattern on the external electrode pattern, opposing ends of the Pd nano-wires, and predetermined positions between the external electrode pattern and the opposing ends of the Pd nano-wires; and Depositing conductive metal on the resin layer pattern and removing the resin layer pattern, thereby electrically connecting the external electrode pattern to the Pd nano-wires.

As set forth above, the present invention can advance the development of the hydrogen sensor, which is essential for the use of hydrogen energy as the next generation energy source. It is regarded that the hydrogen sensor of the present invention can play the key role in the spread of safety technology using hydrogen energy. Through the combination of nano technology and sensor technology, the sensor can have various merits such as low price, micro size and high performance. Based upon the present invention, it is possible to preoccupy component technologies in the domestic market as well as hydrogen sensor technologies in the global level.

BRIEF DESCRIPTION OF THE DRAWINGS

The above and other objects, features and advantages of the present invention will be more apparent from the following detailed description taken in conjunction with the accompanying drawings, in which:

FIGS. 4 to 10 are graphs illustrating the results of hydrogen gas detection using a Pd nano-wire hydrogen sensor, which is manufactured according to the present invention, in which FIG. 4 is the detection result at 20,000 ppm, FIG. 5 is the detection result at 10,000 ppm, FIG. 6 is the detection result at 5,000 ppm, FIG. 7 is the detection result at 1,000 ppm, FIG. 8 is the detection result at 800 ppm, FIG. 9 is the detection result at 200 ppm, and FIG. 10 is the detection result at 20 ppm.

DESCRIPTION OF THE PREFERRED EMBODIMENTS

The present invention will now be described more fully with reference to the accompanying drawings, in which preferred embodiments thereof are shown.

Figure 1:
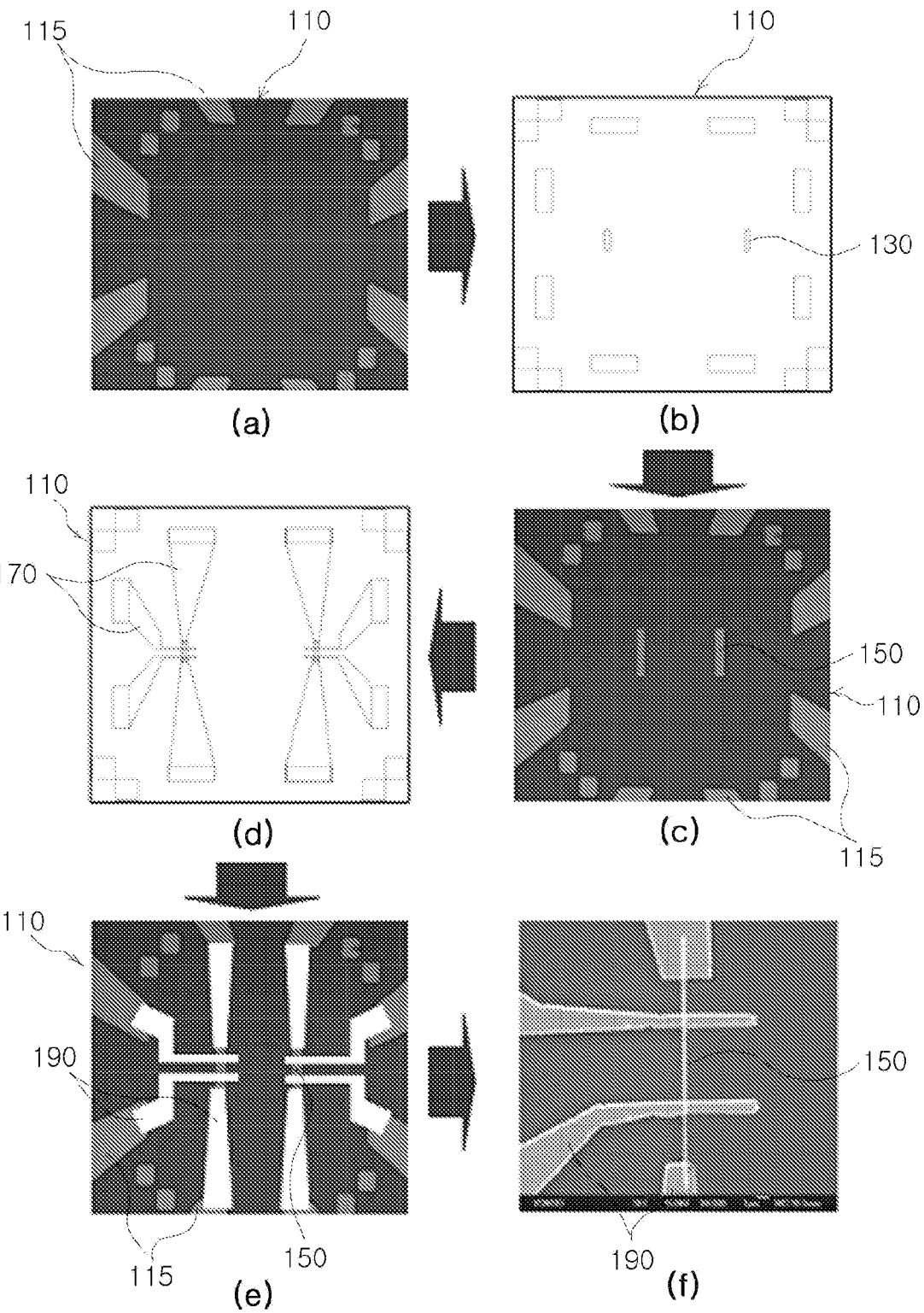
FIG. 1 is a schematic view illustrating a process for manufacturing a Pd nano-wire hydrogen sensor according to an exemplary embodiment of the present invention.

FIG. 1 is a schematic view illustrating a process for manufacturing a hydrogen sensor using Pd nano-wire according to an exemplary embodiment of the present invention.

First, as shown in FIG. 1 (a), an external electrode pattern 115 is formed on a substrate 110. Although the present invention is not limited to kinds of substrate, the substrate is preferably a $SiO_2$ substrate. The external electrode pattern 115 can be formed by depositing conductive metal using a well-known photolithography process. It is preferable that the conductive metal is at least one of Ti and Au.

The external electrode pattern 115 formed as above will be used later as electrodes, through which external current is applied to a device.

Then, as shown in FIG. 1 (b), a resin layer is applied to the substrate 110, and a resin layer nano-channel pattern 130 is formed. Generally, a working area of about 140 $\mu m^2$, where Pd nano-wires will be actually placed, is provided in the center of the substrate 110, where the external electrode pattern 115 is formed. Hence, according to the present invention, the resin layer is applied to the substrate 110 so that the Pd nano-wires can be formed in this working area. Such a resin layer can be formed, for example, by applying polymethyl methacrylate (PMMA) to the substrate and conducting baking at about 170° C. for about 3 min.

Using Computer Aid Design (CAD), a nano-channel pattern of predetermined size is designed in the working area of the substrate, where the resin layer is formed. The pattern is then made into the resin layer nano-channel pattern 130 by an electron beam lithography process.

According to the present invention, it is preferable that the resin layer nano-channel pattern 130 has a linewidth ranging from 100 nm to 500 nm and a length ranging from 10 $\mu m$ to 40 $\mu m$.

Then, as shown in FIG. 1 (c), Pd nano-wires are deposited on the substrate having the nano-channel pattern 130 by sputtering. Here, a Pd deposit has a predetermined thickness, preferably, ranging from 20 nm to 400 nm.

According to the present invention, alloy nano-wires can be more preferably formed by depositing one metal, selected from the group consisting of Ni, Pt and Ag, concurrent with the deposition of the Pd nano-wires. The concurrent deposition of Ni, Pt or Ag with Pd can be realized by a well-known co-sputtering method, and the thickness of the resultant alloy nano-wires is the same as that of the Pd nano-wires. When the alloy nano-wires are formed by the co-sputtering of a hydrogen catalyst, such as Ni, Pt and Al, and Pd, the endurance and reaction time of a resultant sensor can be further improved.

Subsequently, the present invention removes the resin layer using a well-known lift-off process, thereby forming desired Pd nano-wires 150 in the working area of the substrate.

Next, another resin layer is applied to the substrate 110 where the Pd nano-wires 150 are formed. Then, a resin layer pattern 170 is formed on the external electrode pattern 115, opposing ends of the Pd nano-wires 150, and predetermined positions between the external electrode pattern 115 and the opposing ends of the Pd nano-wires 150. That is, as shown in FIG. 1 (d), PMMA is applied again to the substrate, where the Pd nano-wires 150 are formed, followed by baking, and a predetermined pattern is designed using CAD. Then, a typical electron beam lithography process is performed to form the resin layer pattern 170 on the pattern designed as above.

Then, as shown in FIG. 1 (e), a conductive metal layer 190 is deposited on the resin layer pattern 170 by sputtering. Here, the conductive metal layer 190 is preferably made of at least one of Ti and Au. Then, the resin layer pattern is removed using a well-known lift-off process, thereby producing a Pd nano-wire hydrogen sensor, as shown in FIG. 1 (f), where the external electrode pattern 115 is electrically connected to the Pd nano-wires 150. More specifically, the external electrode pattern 115 connected to the opposing ends of the nano-wires 150 acts as input and output electrodes of the hydrogen sensor, located at predetermined positions of the opposing ends of the Pd nano-wires. Also, in the present invention, the external electrode pattern 115 connected between the opposing ends of the Pd nano-wires functions as measuring electrodes to detect hydrogen gas concentration.

In the present invention, preferably, the Pd nano-wires 150 having the aforementioned pattern are subjected to ion milling process in order to maximize the surface area. The ion milling process for Pd nano-wires can be realized by ion-milling the top portion of the substrate, which has the above-mentioned pattern. Preferably, after the sensor pattern is formed, another resin layer is applied to the substrate, and then a resin layer pattern is formed to expose only the Pd nano-wire portions. Subsequently, the exposed Pd nano-wire portions are ion-milled, and thus the resin layer pattern is removed.

Figure 2:
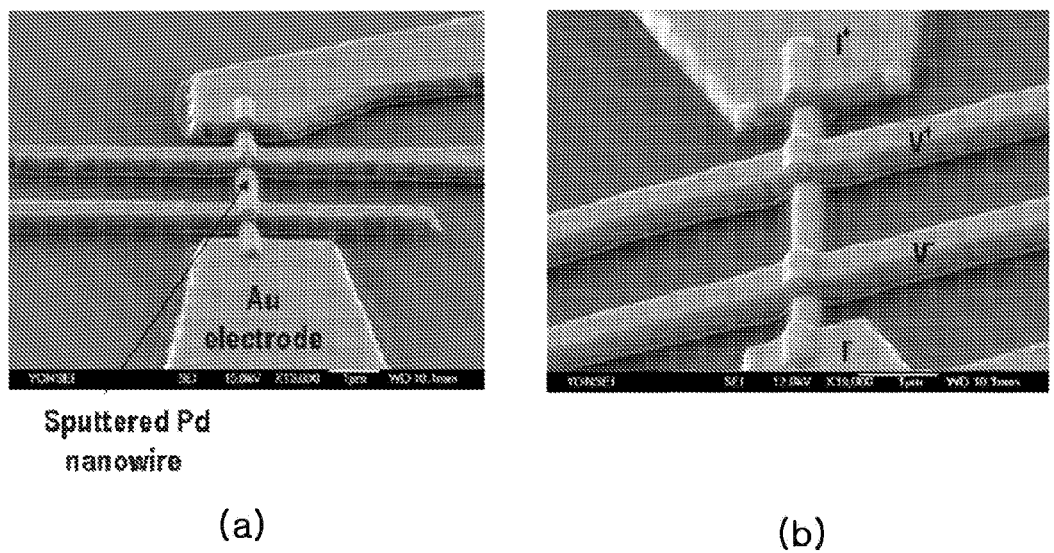
FIG. 2 is SEM pictures illustrating Pd nano-wire hydrogen sensors manufactured according to the exemplary embodiment of the present invention.

FIG. 2 is Scanning Electron Microscope (SEM) pictures illustrating Pd nano-wire hydrogen sensors according to the exemplary embodiment of the present invention, manufactured by the aforementioned process.

The Pd nano-wire hydrogen sensor realized by the above manufacturing process of the present invention has various merits such as detection capability at room temperature, fast detection time, low power consumption and small size. Accordingly, the present invention can produce high efficient hydrogen sensors.

The hydrogen sensor of the present invention can detect a hydrogen gas concentration ranging from 10 ppm to 40,000 ppm, within an error tolerance of 0.01%.

The hydrogen sensor realized by the manufacturing process of the present invention can operate in an ultra-low power mode, consuming electric power below several nanowatts (nWs). Accordingly, the Pd nano-wire hydrogen sensor has merits in terms of the manufacturing process, in which nano-wires can be arranged in desired positions, as well as essential properties as a sensor such as micro size, ultra high sensitivity, operability in an ultra low power mode, and room temperature operability.

Hereinafter, the present invention will be described in detail in conjunction with the following Examples. It is intended, however, that Examples shall be interpreted as illustrative only but not as limiting the scope of the present invention.

EXAMPLES

Au was deposited on a $SiO_2$ substrate using a photolithography process, thereby forming an external electrode pattern. A PMMA resin layer was applied to the substrate, followed by baking at 170° C. for 3 min. A predetermined size of nano-channel pattern was designed, using CAD, in a working area of the substrate, on which the resin layer was formed. Then, a resin layer nano-channel pattern, which has a linewidth ranging from 200 nm to 500 nm and a length ranging from 20 $\mu m$ to 40 $\mu m$, was formed by an electron beam lithography process.

Subsequently, a Pd deposit having a thickness ranging from 20 nm to 400 nm was formed on the substrate having the nano-channel pattern by sputtering, and the resin layer was removed by a well-known lift-off process, thereby forming Pd nano-wires on the substrate. The resin layer was applied again to the substrate having the Pd nano-wires, and a resin layer pattern was formed, by electron beam lithography, on the external electrode pattern, opposing ends of the Pd nano-wires, and predetermined positions between the external electrode pattern and the opposing ends of the Pd nano-wires.

Then, Au was deposited on the resin layer pattern by sputtering, and the resin layer pattern was removed using a well-known lift-off process, thereby producing a Pd nano-wire hydrogen sensor, with the external electrode pattern electrically connected to the Pd nano-wires.

Figure 3:
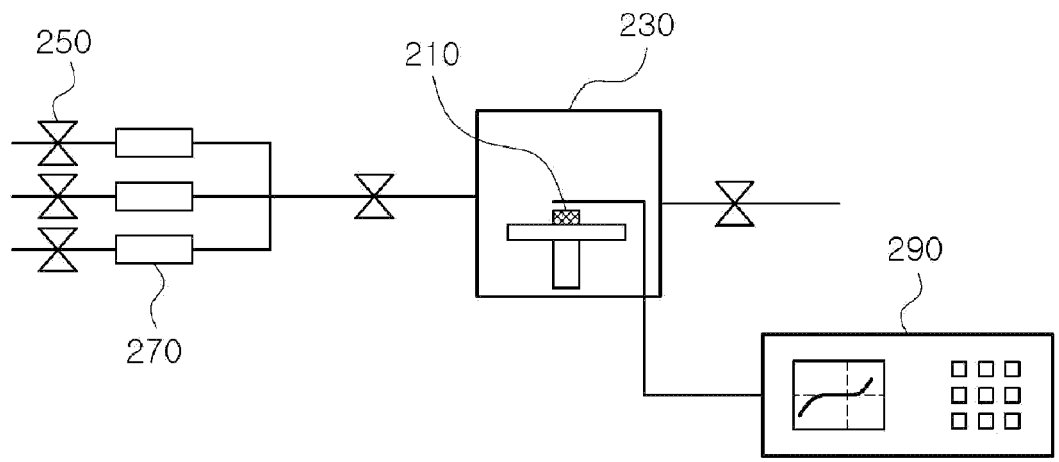
FIG. 3 is a schematic view illustrating a system for measuring the hydrogen detection capability of a Pd nano-wire hydrogen sensor of the present invention.
Figure 4:
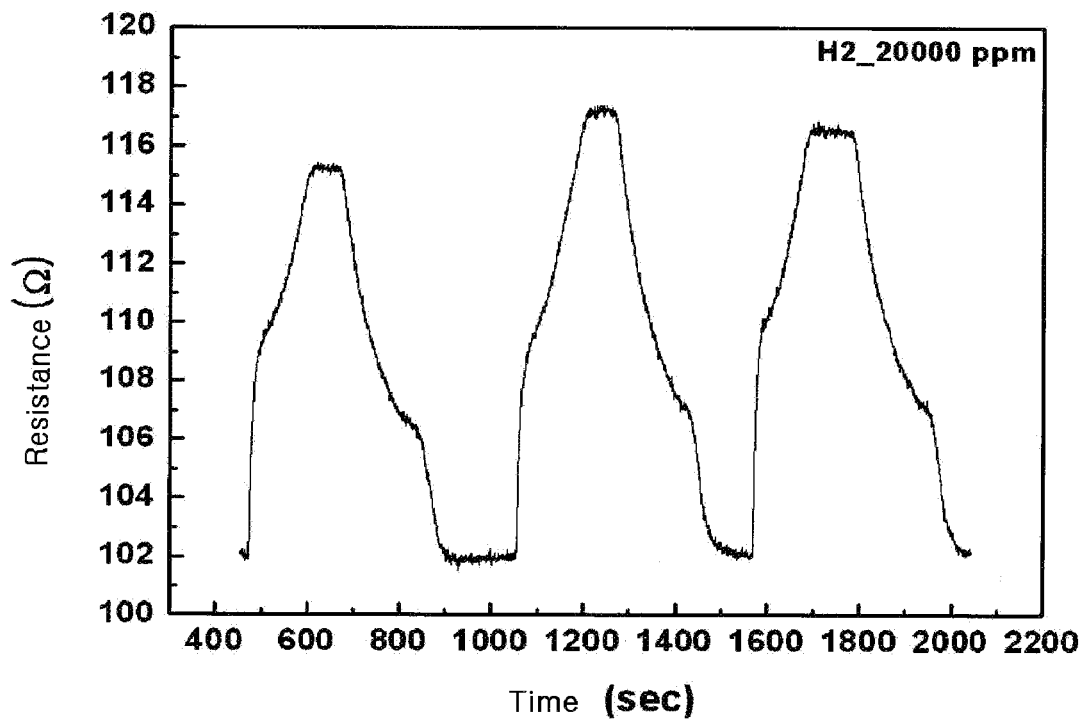
Figure 5:
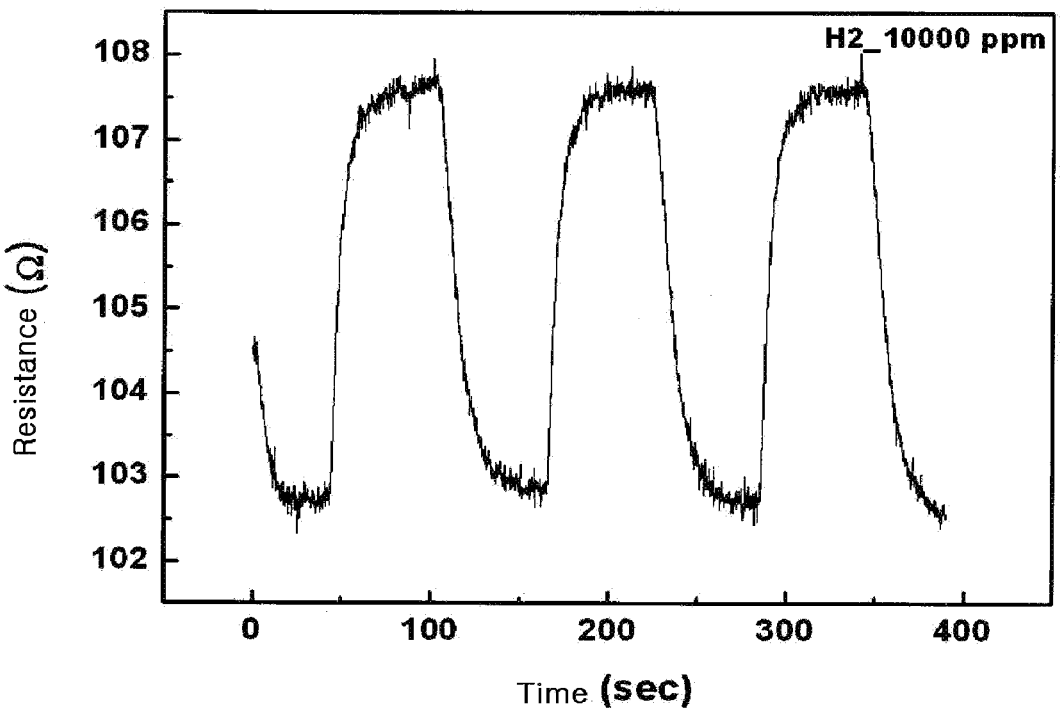
Figure 6:
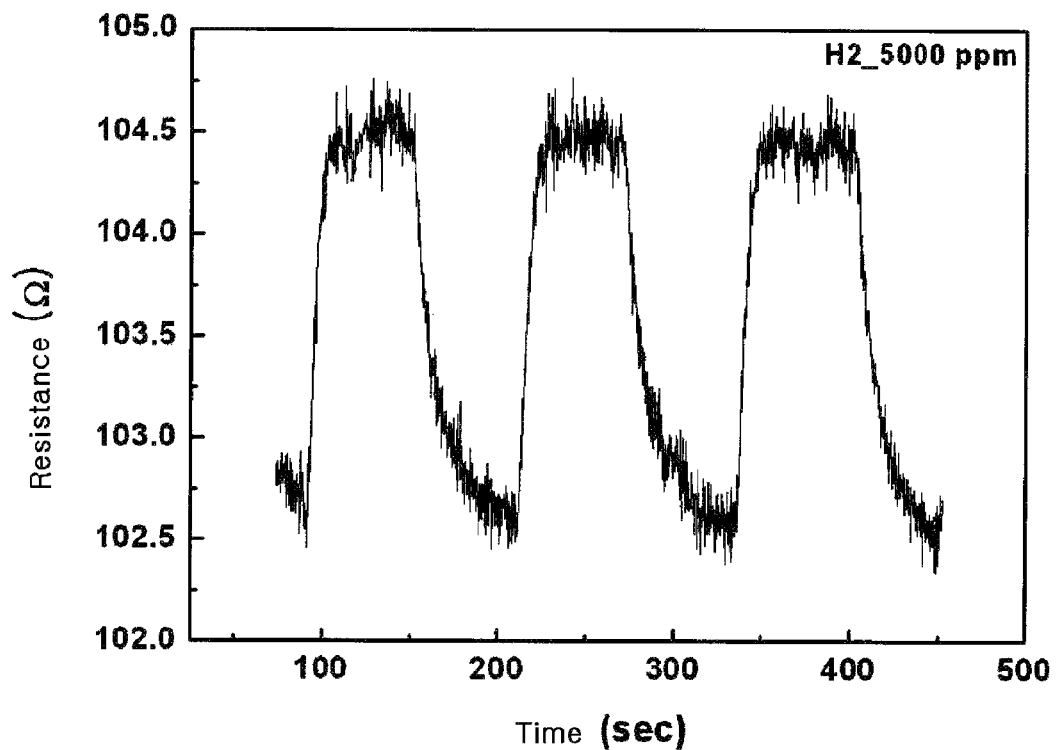
Figure 7:
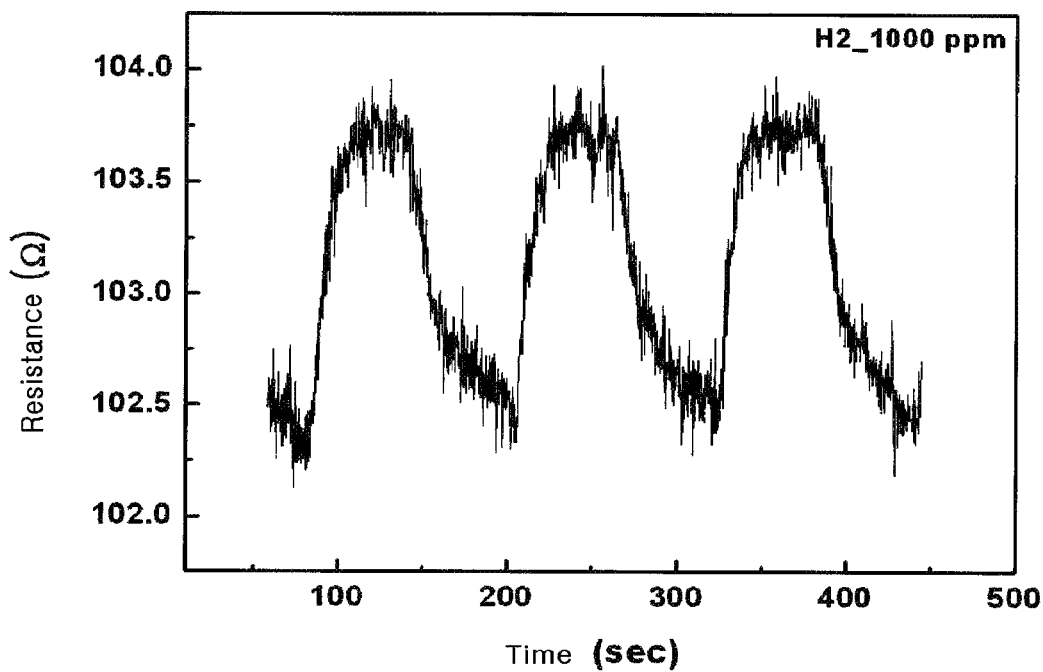
Figure 8:
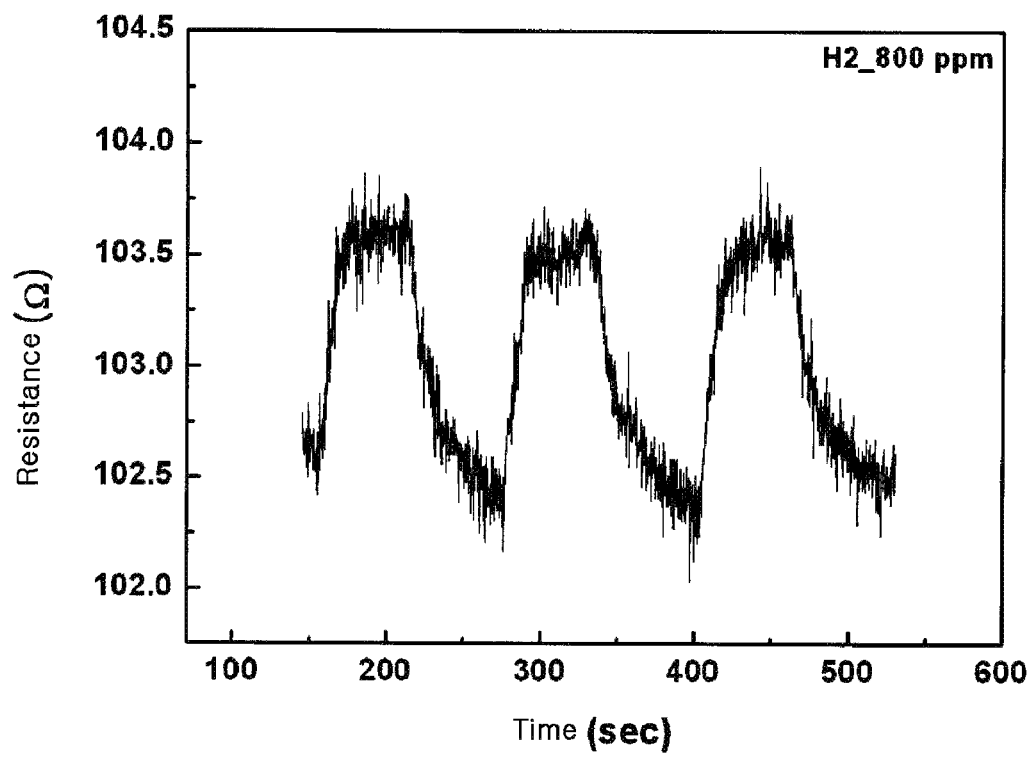
Figure 9:
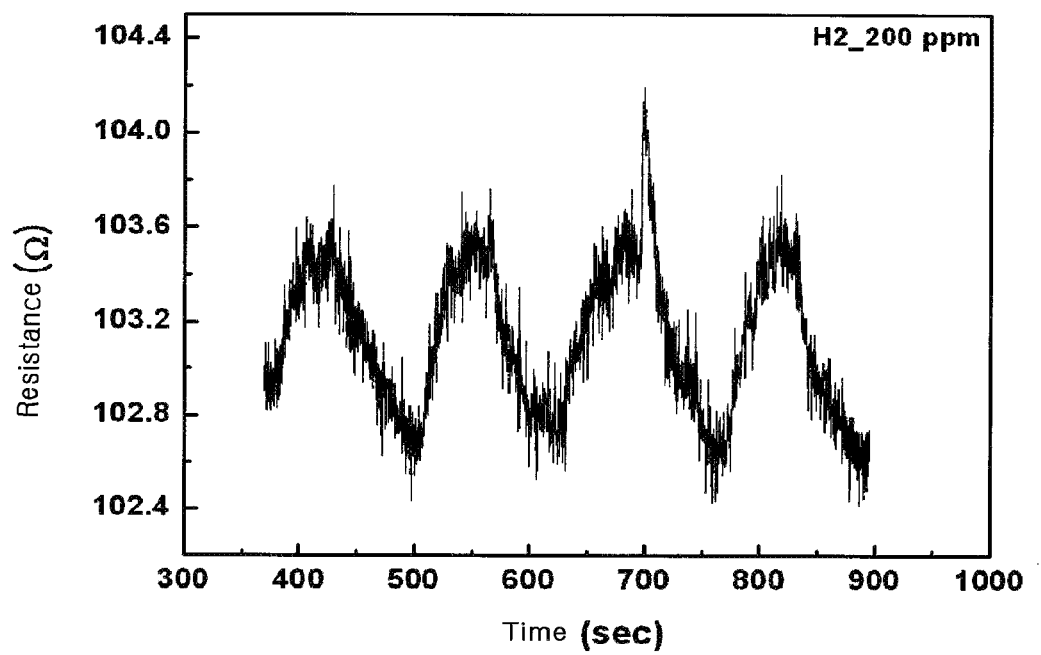
Figure 10:
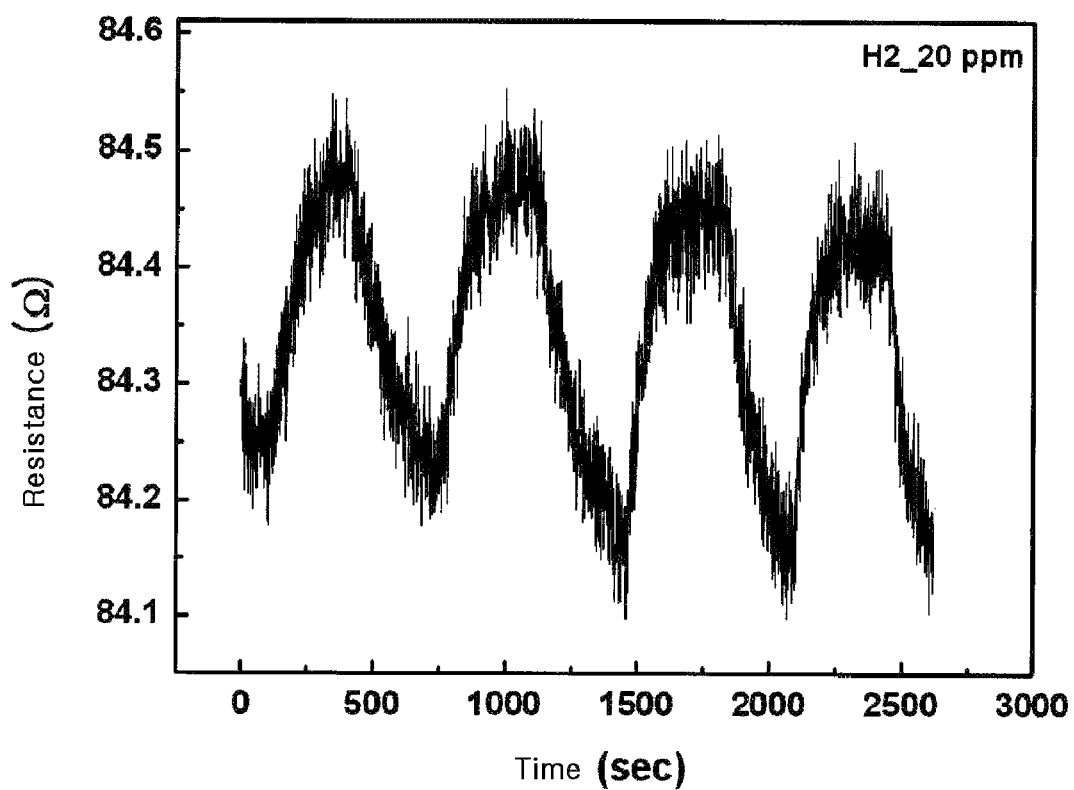

A source measure unit capable of performing measurement using a 4-point probe method was prepared and used in order to evaluate properties of the hydrogen sensor manufactured as above. That is, an evaluation system as shown in FIG. 3 was used to evaluate the hydrogen detection capability of the Pd nano-wire hydrogen sensor. In detail, this evaluation system includes a Pd nano-wire hydrogen sensor 210, a reaction chamber 230, $H_2$ and $N_2$ gas valves 250, Mass Flow Controllers (MFCs) 270 and a current-voltage supply 290.

The reaction chamber 230 also acts to provide a gas atmosphere with desired fractions in order to evaluate the reactivity for actual $H_2$ gas and the electric properties of the resultant sensor device. The $H_2$ and $N_2$ gas valves 250 and the MFCs 270 act to accurately control the composition and ratio of mixed gas ($H_2$:$N_2$) in the reaction chamber 230. In addition, the current-voltage supply 290 serves to detect an electrical signal from the Pd nano-wire hydrogen sensor 210.

When the Pd nano-wires 210 are exposed to hydrogen gas, the hydrogen gas is adsorbed on the Pd nano-wires due to the difference between hydrogen partial pressure around Pd and that of the surface of Pd, and adsorbed $H_2$ molecules decompose into H atoms to lower the surface energy, thereby diffusing into Pd. The diffused H atoms migrate to interstitial sites in a face centered cubic (fcc) structure of Pd ($\alpha$-phase), thereby starting to form $PdH_x$. Then, the hydrogen atoms randomly occupy the interstitial sites (forming an interstitial solid solution), thereby causing strain energy around the H atoms.

If the hydrogen atoms are dissolved in Pd up to the solubility limit, the strain energy increases excessively. In order to lower the strain energy, the hydrogen atoms are regularly rearranged to occupy interstitial sites of Pd ($\beta$-phase) due to the interaction. Accordingly, the hydrogen atoms occupy all of the interstitial sites of Pd. While the crystal structure can be changed occasionally due to the rearrangement of metal atoms, Pd does not change its crystal structure because Pd atoms are not rearranged. Because of the hydrogen atoms occupying the interstitial sites, the migrating electrons experience more scattering to increase resistance, compared to the case where no hydrogen atom exists. Therefore, a difference between resistance values can be obtained according to the existence or absence of the hydrogen atoms.

FIGS. 4 to 10 illustrate the results of hydrogen concentration measurement using the system, shown in FIG. 3, in which a Pd nano-wire hydrogen sensor manufactured according to the present invention is mounted. The measurement was carried out at room temperature, and resistance variations were measured by feeding a mixed gas of 4% $H_2$ and 96% $N_2$ into a sealed chamber, in which a single Pd nano-wire sensor electrically connected to an external current supply was placed, and by applying a current 10 μA to the Pd nano-wire sensor.

The results as shown in FIGS. 4 to 10 were measured by the Pd hydrogen sensor, manufactured according to the present invention, under different hydrogen concentrations such as 10,000 ppm, 5,000 ppm, 1,000 ppm, 800 ppm, 200 ppm and 20 ppm. At a hydrogen concentration of 2%, which is 50% of the upper explosion limit, 14% variation was observed. This variation is remarkably higher than variation values of existing Pd nano-wire sensors, which have been reported up to now. Furthermore, excellent endurance can be observed from the signal magnitude that was maintained substantially the same even after the measurement was repeated several times.

In terms of the amount of hydrogen gas detected in an early stage, which can be regarded as the most important factor of the sensor, the hydrogen sensor of the present invention detected a faint amount of hydrogen 20 ppm in 30 seconds. Also, the hydrogen sensor of the present invention reliably detected a hydrogen concentration difference corresponding to tens of ppm. The hydrogen concentration of 20 ppm is the lowest value, which has ever been detected by existing nanotechnology hydrogen sensors.

Furthermore, the concentration of hydrogen leakage could be correctly found due to excellent linearity of the detection values for the hydrogen concentrations.

While the present invention has been described with reference to the particular embodiments, these particular embodiments are not provided to limit the scope of the present invention. It is to be appreciated that those skilled in the art can improve or modify the embodiments in various forms without departing from the technical scope of the present invention, which will be defined by the appended claims.

What is claimed is:

1. A method for manufacturing a hydrogen sensor using Pd nano-wires, comprising:
    forming an external electrode pattern on a substrate;
    applying a first resin layer to the substrate and forming a resin layer nano-channel pattern;
    depositing Pd on the substrate having the nano-channel pattern by sputtering, and removing the first resin layer to form Pd nano-wires;
    applying a second resin layer to the substrate having the Pd nano-wires, and forming a resin layer pattern on the external electrode pattern, at opposing ends of the Pd nano-wires, and at predetermined positions between the external electrode pattern and the opposing ends of the Pd nano-wires; and
    depositing conductive metal on the resin layer pattern and removing the resin layer pattern, thereby electrically connecting the external electrode pattern to the Pd nano-wires.

2. The method according to claim 1, wherein the conductive metal comprises at least one selected from a group consisting of Au and Ti.

3. The method according to claim 1, wherein the resin layers comprise polymethyl methacrylate.

4. The method according to claim 1, wherein the nano-channel has a linewidth ranging from 100 nm to 500 nm and a length ranging from 10 μm to 40 μm.

5. The method according to claim 1, wherein the Pd deposit, formed by sputtering, has a thickness ranging from 5 nm to 400 nm.

6. The method according to claim 1, wherein the Pd nano-wire hydrogen sensor detects a hydrogen concentration ranging from 10 ppm to 40,000 ppm within an error tolerance of 0.01%.

7. The method according to claim 1, wherein the substrate comprises $SiO_2$.

8. The method according to claim 1, further comprising: ion-milling the Pd nano-wires, which are connected to the external electrode pattern.

9. The method according to claim 1, wherein the Pd nano-wire hydrogen sensor consumes electric power below a few nano watts.

10. The method according to claim 1, further comprising: during the step of depositing Pd, simultaneously depositing at least one metal selected from the group consisting of Ni, Pt and Ag, thereby forming metal alloy nano-wires.

* * * * *